United States Patent
Goldman et al.

(10) Patent No.: US 10,534,008 B2
(45) Date of Patent: *Jan. 14, 2020

(54) MASS SPECTROMETRIC DETERMINATION OF EICOSAPENTAENOIC ACID AND DOCOSAHEXAENOIC ACID

(71) Applicant: Quest Diagnostics Investments Incorporated, Wilmington, DE (US)

(72) Inventors: Scott M. Goldman, Laguna Niguel, CA (US); Julie A. Neidich, Ladera Ranch, CA (US)

(73) Assignee: Quest Diagnostics Investments Incorporated, Wilmington, DE (US)

(*) Notice: Subject to any disclaimer, the term of this patent is extended or adjusted under 35 U.S.C. 154(b) by 0 days.

This patent is subject to a terminal disclaimer.

(21) Appl. No.: 15/635,509

(22) Filed: Jun. 28, 2017

(65) Prior Publication Data

US 2018/0024151 A1 Jan. 25, 2018

Related U.S. Application Data

(63) Continuation of application No. 14/816,586, filed on Aug. 3, 2015, now Pat. No. 9,696,325, which is a continuation of application No. 14/464,336, filed on Aug. 20, 2014, now Pat. No. 9,097,732, which is a continuation of application No. 14/025,503, filed on Sep. 12, 2013, now abandoned, which is a continuation of application No. 13/233,773, filed on Sep. 15, 2011, now Pat. No. 8,557,593.

(60) Provisional application No. 61/383,695, filed on Sep. 16, 2010.

(51) Int. Cl.
| | | |
|---|---|---|
| *G01N 33/92* | (2006.01) | |
| *G01N 33/26* | (2006.01) | |
| *G01N 30/72* | (2006.01) | |
| *H01J 49/00* | (2006.01) | |
| *H01J 49/14* | (2006.01) | |
| *H01J 49/16* | (2006.01) | |

(52) U.S. Cl.
CPC ......... *G01N 33/92* (2013.01); *G01N 30/7266* (2013.01); *G01N 33/26* (2013.01); *H01J 49/004* (2013.01); *H01J 49/0027* (2013.01); *H01J 49/0031* (2013.01); *H01J 49/165* (2013.01); *H01J 49/145* (2013.01); *H01J 49/168* (2013.01); *Y10T 436/104165* (2015.01); *Y10T 436/24* (2015.01); *Y10T 436/25* (2015.01); *Y10T 436/255* (2015.01); *Y10T 436/25125* (2015.01); *Y10T 436/25375* (2015.01)

(58) Field of Classification Search
CPC .... G01N 30/72; G01N 30/7266; G01N 33/26; G01N 33/48; G01N 33/49; G01N 33/92; H01J 49/0027; H01J 49/145; H01J 49/168; H01J 49/0031; H01J 49/004; H01J 49/165; Y10T 436/104165; Y10T 436/24; Y10T 436/25; Y10T 436/25125; Y10T 436/25375; Y10T 436/255

USPC ... 436/63, 71, 161, 173, 174, 175, 177, 178; 250/281, 282

See application file for complete search history.

(56) References Cited

U.S. PATENT DOCUMENTS

| | | |
|---|---|---|
| 5,212,096 A | 5/1993 | Kolhouse et al. |
| 5,772,874 A | 6/1998 | Quinn et al. |
| 5,795,469 A | 8/1998 | Quinn et al. |
| 5,919,368 A | 7/1999 | Quinn et al. |
| 5,968,367 A | 10/1999 | Quinn et al. |
| 8,273,575 B2 | 9/2012 | Goodenowe |
| 8,557,593 B2 | 10/2013 | Goldman et al. |
| 9,097,732 B2 | 8/2015 | Goldman |
| 9,140,686 B2 | 9/2015 | Kamp et al. |
| 9,696,325 B2 * | 7/2017 | Goldman ............... G01N 33/92 |
| 2006/0292607 A1 | 12/2006 | Caprioli |
| 2007/0042953 A1 | 2/2007 | Bazan et al. |
| 2008/0166779 A1 | 7/2008 | Thomas et al. |
| 2011/0020942 A1 | 1/2011 | Cerda et al. |
| 2012/0207800 A1 | 8/2012 | Abu-Baker et al. |

OTHER PUBLICATIONS

Burkard I., et al., "Determination of 24S- and 27-Hydroxycholesterol in Plasma by Highperformance Liquid Chromatography-Mass Spectrometry," Journal of Lipid Research, 2004, vol. 45 (4), pp. 776-781.
Fer M., et al., "Cytochromes P450 from Family 4 Are the Main Omega Hydroxylating Enzymes in Humans: CYP4F3B is the Prominent Player in PUFA Metabolism," Journal of Lipid Research, 2008, vol. 49 (11), pp. 2379-2389.
Final Office Action dated Apr. 12, 2016 for U.S. Appl. No. 14/816,586, filed Aug. 3, 2015.
Final Office Action dated Feb. 20, 2014 for U.S. Appl. No. 14/025,503, filed Sep. 12, 2013.
Gao L., et al., "Novel N-3 Fatty Acid Oxidation Products Activate Nrf2 by Destabilizing the Association between Keap1 and Cullin3," The Journal of Biological Chemistry, 2007, vol. 282 (4), pp. 2529-2537.
Goodenowe D.B., et al., "Peripheral Ethanolamine Plasmalogen Deficiency: A Logical Causative Factor in Alzheimer's Disease and Dementia," Journal of Lipid Research, 2007, vol. 48 (11), pp. 2485-2498.
International Search Report for Application No. PCT/US11/51784, dated Feb. 6, 2012, 3 Pages.
Lacaze J.P., et al., "Soild-Phase Extraction and Liquid Chromatography-Mass Spectrometry for the Determination of Free Fatty Acids in Shellfish," Journal of Chromatography A, 2007, vol. 1145 (1-2), pp. 51-57.
Lawson J.A., et al., "Oxidized Derivatives of Omega-3 Fatty Acids: Identification of IPF3 Alpha-VI in Human Urine," The Journal of Lipid Research, 2006, vol. 47 (11), pp. 2515-2524.
Non-Final Office Action dated Nov. 7, 2013 for U.S. Appl. No. 14/025,503, filed Sep. 12, 2013.

(Continued)

*Primary Examiner* — Maureen Wallenhorst
(74) *Attorney, Agent, or Firm* — Quest Diagnostics

(57) ABSTRACT

The invention relates to the detection of DHA and EPA. In a particular aspect, the invention relates to methods for detecting DHA and EPA by mass spectrometry and kits for carrying out such methods.

12 Claims, 6 Drawing Sheets

(56) References Cited

OTHER PUBLICATIONS

"Non-Final Office Action dated Nov. 14, 2014 for U.S. Appl. No. 14/464,336, filed Aug. 20, 2014".
Non-Final Office Action dated Jan. 22, 2016 for U.S. Appl. No. 14/063,956, filed Oct. 25, 2013.
Non-Final Office Action dated Feb. 25, 2013 for U.S. Appl. No. 13/233,773, filed Sep. 15, 2011.
Non-Final Office Action dated Oct. 25, 2016 for U.S. Appl. No. 14/816,586, filed Aug. 3, 2015.
Non-Final Office Action dated Sep. 21, 2015 for U.S. Appl. No. 14/816,586, filed Aug. 3, 2015.
Rezanka T., "Analysis of Polyunsaturated Fatty Acids Using High Performance Liquid Chromatography—Atmospheric Pressure Chemical Ionization Mass Spectrometry," Journal of High Resolution Chromatography, 2000, vol. 23, pp. 338-342.
Rezanka T., "Analysis of Very Long Chain Polyunsaturated Fatty Acids Using High-Performance Liquid chromatography—Atmospheric Pressure Chemical Ionization Mass Spectrometry," Biochemical Systematics and Ecology, 2000, vol. 28 (9), pp. 847-856.
Salm P., et al., "Simultaneous Quantification of Total Eicosapentaenoic Acid, Docosahexaenoic Acid and Arachidonic Acid in Plasma by High-Performance Liquid Chromatography-Tandem Mass Spectrometry," Biomedical Chromatography, 2011, vol. 25 (6), pp. 652-659.
Williams J., et al., "Quantitative Method for the Profiling of the Endocannabinoid Metabolome by LC Atmospheric Pressure Chemical Ionization-MS," Analytical Chemistry, 2007, vol. 79 (15), pp. 5582-5293.
Wood J.T., et al., "Dietary Docosahexaenoic Acid Supplementation Alters Select Physiological Endocannabinoid-System Metabolites in Brain and Plasma," Journal of Lipid Research, 2010, vol. 51 (6), pp. 1416-1423.
Written Opinion for Application No. PCT/US11/51784, dated Feb. 6, 2012, 5 Pages.
Yin H., et al., "Identification of Novel Autoxidation Products of the .Omega.-3 Fatty Acid Eicosapentaenoic Acid in Vitro and in Vivo," The Journal of Biological Chemistry, 2007, vol. 282 (41), pp. 29890-29901.
Zehethofer N., et al., "Plasma Free Fatty Acid Profiling in a Fish Oil Human Intervention Study Using Ultra-Performance Liquid Chromatography/Electrospray Ionization Tandem Mass Spectrometry," Rapid Communications in Mass Spectrometry, 2008, vol. 22 (13), pp. 2125-2133.
Zimmer D., et al., "Comparison of Turbulent-Flow Chromatography with Automated Solid-Phase Extraction in 96-Well Plates and Liquid-Liquid Extraction Used as Plasma Sample Preparation Techniques for Liquid Chromatography-Tandem Mass Spectrometry," Journal of Chromatography A, 1999, vol. 854, pp. 23-35.

* cited by examiner

MASS SPECTROMETRIC DETERMINATION OF EICOSAPENTAENOIC ACID AND DOCOSAHEXAENOIC ACID

CROSS-REFERENCE TO RELATED APPLICATIONS

This application is a continuation of U.S. application Ser. No. 14/816,586 filed Aug. 3, 2015, now U.S. Pat. No. 9,696,325, which is a continuation of U.S. application Ser. No. 14/464,336 filed Aug. 20, 2014, now U.S. Pat. No. 9,097,732, which is a continuation of U.S. application Ser. No. 14/025,503 filed Sep. 12, 2013, now abandoned, which is a continuation of U.S. application Ser. No. 13/233,773 filed Sep. 15, 2011, now U.S. Pat. No. 8,557,593, which claims the benefit of priority under 35 U.S.C. § 119(e) to U.S. Provisional Application Ser. No. 61/383,695 filed Sep. 16, 2010, each of which is incorporated by reference herein in its entirety.

FIELD OF THE INVENTION

The invention relates to the quantitative measurement of docosahexaenoic acid (DHA) and eicosapentaenoic acid (EPA). In a particular aspect, the invention relates to methods for quantitative measurement of DHA and EPA by APCI-mass spectrometry.

BACKGROUND OF THE INVENTION

Omega-3 fatty acids are a family of unsaturated fatty acids with a carbon-carbon double bond at the third bond from the methyl end of the fatty acid. The human body cannot synthesize omega-3 fatty acids de novo. Instead, they are obtained in the human diet from certain fish, such as cod, mackerel, herring, salmon, and sardines. Nutritionally important omega-3 fatty acids include docosahexaenoic acid (DHA) and eicosapentaenoic acid (EPA). EPA acts as a precursor for prostaglandin-3 (which inhibits platelet aggregation), thromboxane-3, and leukotriene-5. DHA is metabolized to form the docosanoids, which comprise several families of hormones. DHA is also a major fatty acid in sperm and brain phospholipids. High levels of both EPA and DHA have been linked to reduced triglycerides, heart rate, blood pressure, and atherosclerosis. Decreased levels of EPA have been linked to depression and schizophrenia. Decreased levels of DHA have been linked to Alzheimer's disease.

EPA, also sometimes known as timnodonic acid or by the shorthand name 20:5(n-3), is a carboxylic acid with a 20-carbon chain with 5-cis double bonds, the first of which is located at the third carbon from the omega end of the carbon chain. EPA has a molecular mass of approximately 302.451 g/mol.

DHA, also sometimes known as cervonic acid or by the shorthand name 22:6(n-3), is a carboxylic acid with a 22-carbon chain with 6-cis double bonds, the first of which is located at the third carbon from the omega end of the carbon chain. DHA has a molecular mass of approximately 328.488 g/mol.

Quantitation of EPA and DHA by liquid chromatography-mass spectrometry with ESI has been reported. For example Salm, et al., Biomed Chromatogr., 2010, Epub ahead of print, report quantitation of EPA and DHA in plasma by HPLC-ESI (negative ion)-MS/MS; Lacaze, et al., J. Chromatog. A, 2007, 1145:51-57 report methods for quantitating free fatty acids in shellfish tissue extracts with an LC-ESI (negative ion)-MS method; and Zehethofer, et al., Rapid Communications in Mass Spectrom., 2008, 22:2125-33 report quantitating free fatty acids in plasma with an UPLC-ESI (positive ion)-MS/MS method. Other mass spectrometric methods for quantitation of EPA and/or DHA derivatives, metabolites, or oxidation products have also been reported. For example, Řezanka, reports quantitation of EPA and DHA by preparation of methyl esters of EPA and DHA followed by detection of the methyl esters by HPLC-APCI (negative ion)-MS. (See Řezanka, Tomáš, J. High Resol. Chromatogr. 2000, 23:338-42 (EPA and DHA in linseed oil and prepared standards); and Řezanka, Tomáš, Biochemical Systematics and Ecology 2000, 28:847-56 (EpA and DHA in three freshwater crustacean species.) Additionally, Fer, et al., J. Lipid Research 2008, 49:2379-89, reports detection of ω- and (ω-1)hydroxylated derivatives of EPA and DHA by an HPLC-APCI (negative ion)-MS method; Yin, et al., J. Biol. Chem. 2007, 282:29890-901, report detection of autoxidation products of EPA and DHA by an HPLC-APCI (negative ion)-MS method; Lawson, et al., J. Lipid Research 2006, 47:2515-24, and Gao, et al., J. Biol. Chem. 2007, 282:2529-37, report detection of oxidized derivatives of EPA and DHA with LC-ESI (negative ion)-MS/MS.

SUMMARY OF THE INVENTION

The present invention provides methods for detecting the amount of DHA and/or EPA in a sample by mass spectrometry.

In one aspect, the invention provides methods for determining the amount of DHA in a sample by mass spectrometry. In some embodiments, the methods include the steps of: (i) subjecting DHA in the sample to an atmospheric pressure chemical ionization (APCI) source to generate one or more DHA ions detectable by mass spectrometry; (ii) determining the amount of one or more DHA ions by mass spectrometry; and (iii) relating the amount of one or more DHA ions to the amount of DHA in the sample. In some embodiments, one or more DHA ions comprise an ion with a mass to charge ratio (m/z) of about 327.2±0.5. In some embodiments, the sample comprises a sample derived from a human, such as a human body fluid, such as plasma or serum. In some embodiments, the method has a limit of detection for DHA in human serum of about 5 μmol/L or less. In some embodiments, the method further comprises simultaneously determining the amount of EPA in the sample by: (i) subjecting eicosapentaenoic acid (EPA) in the sample to the APCI source to generate one or more EPA ions detectable by mass spectrometry; (ii) determining the amount of one or more EPA ions by mass spectrometry; and (iii) relating the amount of one or more EPA ions to the amount of a EPA in the sample.

In a second aspect, the invention provides methods for determining the amount of EPA in a sample by mass spectrometry. In some embodiments, the methods include the steps of: (i) subjecting EPA in the sample to an APCI source to generate one or more EPA ions detectable by mass spectrometry; (ii) determining the amount of one or more EPA ions by mass spectrometry; and (iii) relating the amount of one or more EPA ions to the amount of EPA in the sample. In some embodiments, one or more EPA ions comprise an ion with a mass to charge ratio (m/z) of about 301.2±0.5. In some embodiments, the sample comprises a sample derived from a human, such as a human body fluid, such as plasma or serum. In some embodiments, the method has a limit of detection for EPA in human serum of about 10 μmol/L or less. In some embodiments, the method further comprises simultaneously determining the amount of EPA in said sample by: (i) subjecting eicosapentaenoic acid (EPA) in the sample to the APCI source to generate one or more EPA ions detectable by mass spectrometry; (ii) determining the amount of said one or more EPA ions by mass spectrometry; and (iii) relating the amount of one or more EPA ions to the amount of a DHA in the sample.

In some embodiments of either of the above two aspects, the APCI ionization source is operated in negative ionization mode. In some embodiments, DHA and/or EPA in a sample are subjected to a hydrolyzing agent, such as an acid, prior to ionization. In some embodiments, DHA and/or EPA in a sample are subjected to liquid/liquid extraction prior to ionization. In some embodiments, DHA and/or EPA in a sample are subjected to liquid chromatography column, such as a high performance liquid chromatography column, prior to ionization.

In a third aspect, the invention provides methods for determining the amount of docosahexaenoic acid (DHA), eicosapentaenoic acid (EPA), or both in a plasma or serum sample from a human patient, comprising: (i) subjecting a serum sample to a hydrolyzing agent to generate a hydrolyzed sample; (ii) purifying DHA and/or EPA in the hydrolyzed sample; (iii) subjecting the purified DHA and/or EPA to an ionization source in negative ion mode to generate one or more DHA and/or EPA ions detectable by mass spectrometry; (iv) determining the amount of one or more DHA and/or EPA ions by mass spectrometry; and (v) relating the amount of DHA and/or EPA ions to the amount of a DHA and/or EPA in the sample. In some embodiments, the step of purifying comprises subjecting DHA and/or EPA in said hydrolyzed sample to liquid/liquid extraction. In some embodiments, the step of purifying comprises subjecting DHA and/or EPA in said hydrolyzed sample to liquid chromatography. In some embodiments, the ionization source is APCI. In some embodiments, one or more DHA ions comprise an ion with a mass to charge ratio of 327.2±0.5. In some embodiments, one or more EPA ions comprise an ion with a mass to charge ratio of 301.2±0.5. In some embodiments, DHA and EPA are simultaneously determined in the human serum sample.

In the some embodiments of the methods described herein, mass spectrometry is not conducted by tandem mass spectrometry. In these methods, mass spectrometry may be single mass spectrometry conducted by any method known in the art including single ion monitoring or collecting all data over a range of mass to charge ratios (i.e., scanning). In some embodiments, mass spectrometry may be conducted by tandem mass spectrometry. In embodiments utilizing tandem mass spectrometry, tandem mass spectrometry may be conducted by any method known in the art, including for example, multiple reaction monitoring, precursor ion scanning, or product ion scanning.

In embodiments which utilize two or more of an extraction column, an analytical column, and an ionization source, two or more of these components may be connected in an on-line fashion to allow for automated sample processing and analysis.

In embodiments where a sample comprises both EPA and DHA, both analytes in a sample may be ionized and/or detected simultaneously. As used herein, the term "simultaneous" as applied to simultaneously ionizing and/or detecting the amount of two or more analytes from a sample means ionizing two or more analytes and/or acquiring data reflective of the amount of the two or more analytes in the sample from the same sample injection. The data for each analyte may be acquired sequentially or in parallel, depending on the instrumental techniques employed. For example, a single sample containing two analytes may be injected into an on-line HPLC column, which may then elute each analyte one after the other, resulting in introduction of the analytes into a mass spectrometer sequentially. Determining the amount of each of these two analytes is simultaneous for the purposes herein, as both analytes result from the same sample injection into the HPLC.

In some embodiments, EPA ions detected by mass spectrometry comprise ions with a mass/charge ratio (m/z) of 301.2±0.5, and DHA ions detected by mass spectrometry comprise ions with a mass/charge ratio (m/z) of 327.2±0.5.

EPA and DHA may be found in the circulation of an animal and/or may be generated by a biological organism, such as a plant, an animal, or single-celled organism. As such, preferred samples may be biological samples; particularly biological fluid samples such as serum or plasma. In some embodiments, the biological samples may be derived from a human patient having or at risk to develop any of the following conditions: pregnancy, cardiac disease, cancer, Alzheimer's, infant cognitive development deficiencies, infant visual development deficiencies, postpartum depression, dementia, and hypertension.

As used herein, "derivatizing" means reacting two or more molecules to form a new molecule. As used herein, the names of derivatized forms of compounds (including fatty acids such as EPA and DHA) include an indication as to the nature of derivatization. For example, the methyl esters of EPA and DHA would be referred to as EPA-methyl ester and DHA-methyl ester.

Mass spectrometry may be performed in negative ion mode. Alternatively, mass spectrometry may be performed in positive ion mode. Various ionization sources, including for example atmospheric pressure chemical ionization (APCI), laser diode thermal desorption (LDTD), or electrospray ionization (ESI), may be used in embodiments of the present invention. In certain preferred embodiments, EPA and DHA are measured using APCI in negative ion mode.

In preferred embodiments, one or more separately detectable internal standards are provided in the sample, the amount of which are also determined in the sample. In these embodiments, all or a portion of both the analyte(s) of interest and the internal standard(s) present in the sample are ionized to produce a plurality of ions detectable in a mass spectrometer, and one or more ions produced from each analyte of interest and internal standard are detected by mass spectrometry. Exemplary internal standards for EPA and DHA include EPA-$^2H_5$ and DHA-$^2H_5$, respectively.

Ions detectable in a mass spectrometer may be generated for each of the exemplary internal standards listed above. Exemplary spectra generated demonstrating detection of EPA-$^2H_5$ and DHA-$^2H_5$ are discussed in Example 4, and shown in FIGS. 3 and 4, respectively.

As used herein, an "isotopic label" produces a mass shift in the labeled molecule relative to the unlabeled molecule when analyzed by mass spectrometric techniques. Examples of suitable labels include deuterium (d or $^2H$), $^{13}C$, and $^{15}N$. For example, EPA-$^2H_5$ and DHA-$^2H_5$ have masses of about 5 mass units higher than EPA and DHA. The isotopic label can be incorporated at one or more positions in the molecule and one or more kinds of isotopic labels can be used on the same isotopically labeled molecule.

In other embodiments, the amount of DHA and/or EPA ions may be determined by comparison to one or more external reference standards. Exemplary external reference standards include blank plasma or serum spiked with one or more of DHA-$^2$H$_5$ and EPA-$^2$H$_5$. External standards typically will undergo the same treatment and analysis as any other sample to be analyzed.

In certain embodiments, the lower limit of quantitation (LLOQ) of DHA is less than 10 μmol/L; such as between about 10 μmol/L and 0.91 μmol/L; such as between about 5 μmol/L and 0.91 μmol/L; such as between about 2 μmol/L and 0.91 μmol/L; such as about 0.91 μmol/L. In certain embodiments, the lower limit of quantitation (LLOQ) of EPA is less than 20 μmol/L; such as between about 20 μmol/L and 2.28 μmol/L; such as between about 10 μmol/L and 2.28 μmol/L; such as between about 5 μmol/L and 2.28 μmol/L; such as about 2.28 μmol/L.

In certain embodiments, the limit of detection (LOD) of DHA is less than 5 μmol/L; such as between about 5 μmol/L and 0.25 μmol/L; such as between about 2 μmol/L and 0.25 μmol/L; such as between about 1 μmol/L and 0.25 μmol/L; such as between about 0.5 μmol/L and 0.25 μmol/L; such as about 0.25 μmol/L. In certain embodiments, the limit of detection (LOD) of EPA is less than 10 μmol/L; such as between about 10 μmol/L and 0.67 μmol/L; such as between about 5 μmol/L and 0.67 μmol/L; such as between about 2 μmol/L and 0.67 μmol/L; such as between about 1 μmol/L and 0.67 μmol/L; such as about 0.67 μmol/L.

As used herein, unless otherwise stated, the singular forms "a," "an," and "the" include plural reference. Thus, for example, a reference to "a protein" includes a plurality of protein molecules.

As used herein, the term "purification" or "purifying" does not refer to removing all materials from the sample other than the analyte(s) of interest. Instead, purification refers to a procedure that enriches the amount of one or more analytes of interest relative to other components in the sample that may interfere with detection of the analyte of interest. Purification of the sample by various means may allow relative reduction of one or more interfering substances, e.g., one or more substances that may or may not interfere with the detection of selected parent or daughter ions by mass spectrometry. Relative reduction as this term is used does not require that any substance, present with the analyte of interest in the material to be purified, is entirely removed by purification.

As used herein, the term "solid phase extraction" or "SPE" refers to a process in which a chemical mixture is separated into components as a result of the affinity of components dissolved or suspended in a solution (i.e., mobile phase) for a solid through or around which the solution is passed (i.e., solid phase). In some instances, as the mobile phase passes through or around the solid phase, undesired components of the mobile phase may be retained by the solid phase resulting in a purification of the analyte in the mobile phase. In other instances, the analyte may be retained by the solid phase, allowing undesired components of the mobile phase to pass through or around the solid phase. In these instances, a second mobile phase is then used to elute the retained analyte off of the solid phase for further processing or analysis. SPE, including TFLC, may operate via a unitary or mixed mode mechanism. Mixed mode mechanisms utilize ion exchange and hydrophobic retention in the same column; for example, the solid phase of a mixed-mode SPE column may exhibit strong anion exchange and hydrophobic retention; or may exhibit column exhibit strong cation exchange and hydrophobic retention.

As used herein, the term "chromatography" refers to a process in which a chemical mixture carried by a liquid or gas is separated into components as a result of differential distribution of the chemical entities as they flow around or over a stationary liquid or solid phase.

As used herein, the term "liquid chromatography" or "LC" means a process of selective retardation of one or more components of a fluid solution as the fluid uniformly percolates through a column of a finely divided substance, or through capillary passageways. The retardation results from the distribution of the components of the mixture between one or more stationary phases and the bulk fluid, (i.e., mobile phase), as this fluid moves relative to the stationary phase(s). Examples of "liquid chromatography" include reverse phase liquid chromatography (RPLC), high performance liquid chromatography (HPLC), and turbulent flow liquid chromatography (TFLC) (sometimes known as high turbulence liquid chromatography (HTLC) or high throughput liquid chromatography).

As used herein, the term "high performance liquid chromatography" or "HPLC" (sometimes known as "high pressure liquid chromatography") refers to liquid chromatography in which the degree of separation is increased by forcing the mobile phase under pressure through a stationary phase, typically a densely packed column.

As used herein, the term "turbulent flow liquid chromatography" or "TFLC" (sometimes known as high turbulence liquid chromatography or high throughput liquid chromatography) refers to a form of chromatography that utilizes turbulent flow of the material being assayed through the column packing as the basis for performing the separation. TFLC has been applied in the preparation of samples containing two unnamed drugs prior to analysis by mass spectrometry. See, e.g., Zimmer et al., *J Chromatogr A* 854: 23-35 (1999); see also, U.S. Pat. Nos. 5,968,367, 5,919,368, 5,795,469, and 5,772,874, which further explain TFLC. Persons of ordinary skill in the art understand "turbulent flow". When fluid flows slowly and smoothly, the flow is called "laminar flow". For example, fluid moving through an HPLC column at low flow rates is laminar. In laminar flow the motion of the particles of fluid is orderly with particles moving generally in straight lines. At faster velocities, the inertia of the water overcomes fluid frictional forces and turbulent flow results. Fluid not in contact with the irregular boundary "outruns" that which is slowed by friction or deflected by an uneven surface. When a fluid is flowing turbulently, it flows in eddies and whirls (or vortices), with more "drag" than when the flow is laminar. Many references are available for assisting in determining when fluid flow is laminar or turbulent (e.g., *Turbulent Flow Analysis: Measurement and Prediction*, P. S. Bernard & J. M. Wallace, John Wiley & Sons, Inc., (2000); *An Introduction to Turbulent Flow*, Jean Mathieu & Julian Scott, Cambridge University Press (2001)).

As used herein, the term "gas chromatography" or "GC" refers to chromatography in which the sample mixture is vaporized and injected into a stream of carrier gas (as nitrogen or helium) moving through a column containing a stationary phase composed of a liquid or a particulate solid and is separated into its component compounds according to the affinity of the compounds for the stationary phase.

As used herein, the term "large particle column" or "extraction column" refers to a chromatography column containing an average particle diameter greater than about 50 μm.

As used herein, the term "analytical column" refers to a chromatography column having sufficient chromatographic plates to effect a separation of materials in a sample that elute from the column sufficient to allow a determination of the presence or amount of an analyte. In a preferred embodiment the analytical column contains particles of about 5 µm in diameter. Such columns are often distinguished from "extraction columns", which have the general purpose of separating or extracting retained material from non-retained materials in order to obtain a purified sample for further analysis.

As used herein, the terms "on-line" and "inline", for example as used in "on-line automated fashion" or "on-line extraction" refers to a procedure performed without the need for operator intervention. In contrast, the term "off-line" as used herein refers to a procedure requiring manual intervention of an operator. Thus, if samples are subjected to precipitation, and the supernatants are then manually loaded into an autosampler, the precipitation and loading steps are off-line from the subsequent steps. In various embodiments of the methods, one or more steps may be performed in an on-line automated fashion.

As used herein, the term "mass spectrometry" or "MS" refers to an analytical technique to identify compounds by their mass. MS refers to methods of filtering, detecting, and measuring ions based on their mass-to-charge ratio, or "m/z". MS technology generally includes (1) ionizing the compounds to form charged species; and (2) detecting the charged species based on their mass-to-charge ratio. The compounds may be ionized and detected by any suitable means. A "mass spectrometer" generally includes an ionizer and an ion detector. In general, one or more molecules of interest are ionized, and the ions are subsequently introduced into a mass spectrometric instrument where, due to a combination of magnetic and electric fields, the ions follow a path in space that is dependent upon mass ("m") and charge ("z"). See, e.g., U.S. Pat. No. 6,204,500, entitled "Mass Spectrometry From Surfaces;" U.S. Pat. No. 6,107,623, entitled "Methods and Apparatus for Tandem Mass Spectrometry;" U.S. Pat. No. 6,268,144, entitled "DNA Diagnostics Based On Mass Spectrometry;" U.S. Pat. No. 6,124,137, entitled "Surface-Enhanced Photolabile Attachment And Release For Desorption And Detection Of Analytes;" Wright et al., *Prostate Cancer and Prostatic Diseases* 1999, 2: 264-76; and Merchant and Weinberger, *Electrophoresis* 2000, 21: 1164-67.

As used herein, the term "operating in negative ion mode" refers to those mass spectrometry methods where negative ions are generated and detected. The term "operating in positive ion mode" as used herein, refers to those mass spectrometry methods where positive ions are generated and detected.

As used herein, the term "ionization" or "ionizing" refers to the process of generating an analyte ion having a net electrical charge equal to one or more electron units. Negative ions are those having a net negative charge of one or more electron units, while positive ions are those having a net positive charge of one or more electron units.

As used herein, the term "electron ionization" or "EI" refers to methods in which an analyte of interest in a gaseous or vapor phase interacts with a flow of electrons. Impact of the electrons with the analyte produces analyte ions, which may then be subjected to a mass spectrometry technique.

As used herein, the term "chemical ionization" or "CI" refers to methods in which a reagent gas (e.g. ammonia) is subjected to electron impact, and analyte ions are formed by the interaction of reagent gas ions and analyte molecules.

As used herein, the term "fast atom bombardment" or "FAB" refers to methods in which a beam of high energy atoms (often Xe or Ar) impacts a non-volatile sample, desorbing and ionizing molecules contained in the sample. Test samples are dissolved in a viscous liquid matrix such as glycerol, thioglycerol, m-nitrobenzyl alcohol, 18-crown-6 crown ether, 2-nitrophenyloctyl ether, sulfolane, diethanolamine, and triethanolamine. The choice of an appropriate matrix for a compound or sample is an empirical process.

As used herein, the term "matrix-assisted laser desorption ionization" or "MALDI" refers to methods in which a non-volatile sample is exposed to laser irradiation, which desorbs and ionizes analytes in the sample by various ionization pathways, including photo-ionization, protonation, deprotonation, and cluster decay. For MALDI, the sample is mixed with an energy-absorbing matrix, which facilitates desorption of analyte molecules.

As used herein, the term "surface enhanced laser desorption ionization" or "SELDI" refers to another method in which a non-volatile sample is exposed to laser irradiation, which desorbs and ionizes analytes in the sample by various ionization pathways, including photo-ionization, protonation, deprotonation, and cluster decay. For SELDI, the sample is typically bound to a surface that preferentially retains one or more analytes of interest. As in MALDI, this process may also employ an energy-absorbing material to facilitate ionization.

As used herein, the term "electrospray ionization" or "ESI," refers to methods in which a solution is passed along a short length of capillary tube, to the end of which is applied a high positive or negative electric potential. Solution reaching the end of the tube is vaporized (nebulized) into a jet or spray of very small droplets of solution in solvent vapor. This mist of droplets flows through an evaporation chamber, which is heated slightly to prevent condensation and to evaporate solvent. As the droplets get smaller the electrical surface charge density increases until such time that the natural repulsion between like charges causes ions as well as neutral molecules to be released.

As used herein, the term "atmospheric pressure chemical ionization" or "APCI," refers to mass spectrometry methods that are similar to ESI; however, APCI produces ions by ion-molecule reactions that occur within a plasma at atmospheric pressure. The plasma is maintained by an electric discharge between the spray capillary and a counter electrode. Then ions are typically extracted into the mass analyzer by use of a set of differentially pumped skimmer stages. A counterflow of dry and preheated $N_2$ gas may be used to improve removal of solvent. The gas-phase ionization in APCI can be more effective than ESI for analyzing less-polar species.

The term "atmospheric pressure photoionization" or "APPI" as used herein refers to the form of mass spectrometry where the mechanism for the photoionization of molecule M is photon absorption and electron ejection to form the molecular ion M+. Because the photon energy typically is just above the ionization potential, the molecular ion is less susceptible to dissociation. In many cases it may be possible to analyze samples without the need for chromatography, thus saving significant time and expense. In the presence of water vapor or protic solvents, the molecular ion can extract H to form MH+. This tends to occur if M has a high proton affinity. This does not affect quantitation accuracy because the sum of M+ and MH+ is constant. Drug compounds in protic solvents are usually observed as MH+, whereas nonpolar compounds such as naphthalene or testosterone usually form M+. See, e.g., Robb et al., *Anal. Chem.* 2000, 72(15): 3653-3659.

As used herein, the term "inductively coupled plasma" or "ICP" refers to methods in which a sample interacts with a partially ionized gas at a sufficiently high temperature such that most elements are atomized and ionized.

As used herein, the term "desorption" refers to the removal of an analyte from a surface and/or the entry of an analyte into a gaseous phase. Laser diode thermal desorption (LDTD) is a technique wherein a sample containing the analyte is thermally desorbed into the gas phase by a laser pulse. The laser hits the back of a specially made 96-well plate with a metal base. The laser pulse heats the base and the heat causes the sample to transfer into the gas phase. The gas phase sample may then be drawn into an ionization source, where the gas phase sample is ionized in preparation for analysis in the mass spectrometer. When using LDTD, ionization of the gas phase sample may be accomplished by any suitable technique known in the art, such as by ionization with a corona discharge (for example by APCI).

As used herein, the term "field desorption" refers to methods in which a non-volatile test sample is placed on an ionization surface, and an intense electric field is used to generate analyte ions.

As used herein, the term "selective ion monitoring" is a detection mode for a mass spectrometric instrument in which only ions within a relatively narrow mass range, typically about one mass unit, are detected.

As used herein, "multiple reaction mode," sometimes known as "selected reaction monitoring," is a detection mode for a mass spectrometric instrument in which a precursor ion and one or more fragment ions are selectively detected.

As used herein, the term "lower limit of quantification", "lower limit of quantitation" or "LLOQ" refers to the point where measurements become quantitatively meaningful. The analyte response at this LLOQ is identifiable, discrete and reproducible with a concentration at which the standard deviation (SD) is less than one third of the total allowable error (TEa; arbitrarily set for DHA and EPA as 22% of the LLOQ).

As used herein, the term "limit of detection" or "LOD" is the point at which the measured value is larger than the uncertainty associated with it. The LOD is the point at which a value is beyond the uncertainty associated with its measurement and is defined as the mean of the blank plus four times the standard deviation of the blank.

As used herein, an "amount" of an analyte in a body fluid sample refers generally to an absolute value reflecting the mass of the analyte detectable in volume of sample. However, an amount also contemplates a relative amount in comparison to another analyte amount. For example, an amount of an analyte in a sample can be an amount which is greater than a control or normal level of the analyte normally present in the sample.

The term "about" as used herein in reference to quantitative measurements not including the measurement of the mass of an ion, refers to the indicated value plus or minus 10%. Mass spectrometry instruments can vary slightly in determining the mass of a given analyte. The term "about" in the context of the mass of an ion or the mass/charge ratio of an ion refers to +/−0.50 atomic mass unit.

The summary of the invention described above is non-limiting and other features and advantages of the invention will be apparent from the following detailed description of the invention, and from the claims.

DETAILED DESCRIPTION OF THE INVENTION

Figure 1:
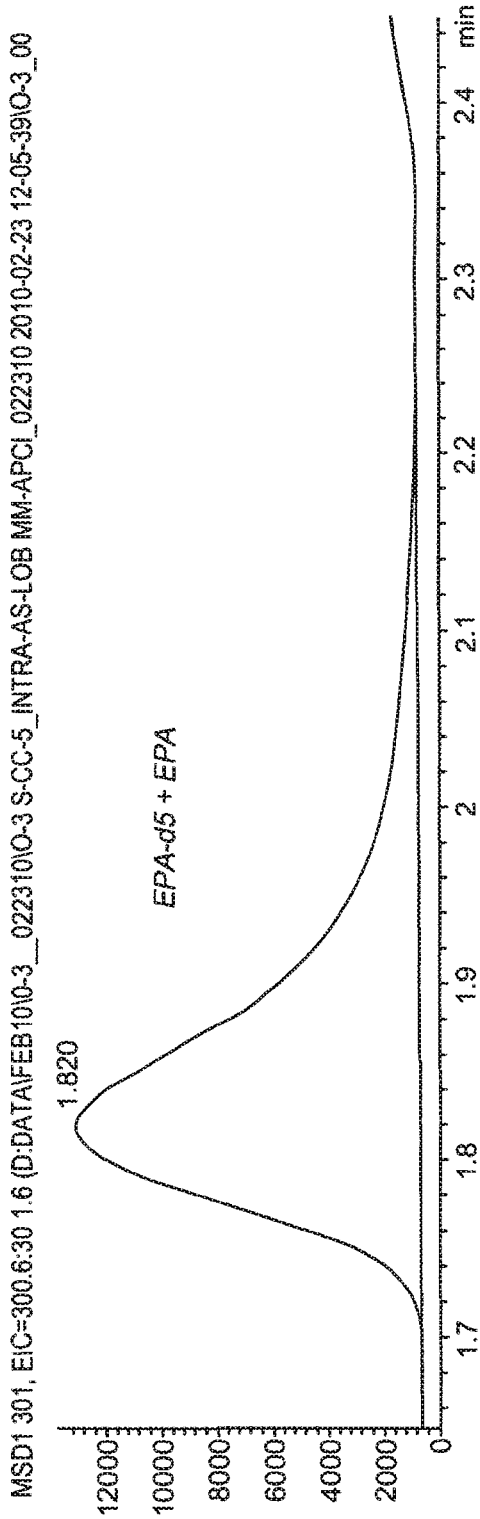
FIG. 1 shows an exemplary chromatogram for EPA/EPA-$^2$H$_5$ (internal standard). Details are discussed in Example 4.

Methods are described for measuring EPA and/or DHA in a sample. More specifically, mass spectrometric methods are described for detecting and quantifying EPA and/or DHA in a sample. The methods may utilize APCI to ionize underivatized EPA and/or DHA in the sample prior to detection by mass spectrometry.

The methods may use an on-line analytical liquid chromatography technique, such as high performance liquid chromatography (HPLC), to perform a purification of DHA and/or EPA, combined with methods of mass spectrometry (MS), thereby providing a high-throughput assay system for detecting and quantifying DHA and/or EPA in a sample. Preferred embodiments are particularly well suited for application in large clinical laboratories for automated DHA and/or EPA quantitation.

Suitable test samples for use in methods of the present invention include any test sample that may contain the analyte of interest. In some preferred embodiments, a sample is a biological sample; that is, a sample obtained from any biological source, such as an animal, a cell culture, an organ culture, etc. In certain preferred embodiments, samples are obtained from a mammalian animal, such as a dog, cat, horse, etc. Particularly preferred mammalian animals are primates, most preferably male or female humans. Preferred samples comprise bodily fluids such as blood, plasma, serum, saliva, cerebrospinal fluid, or tissue samples; preferably plasma (including EDTA and heparin plasma) and serum; most preferably serum. Such samples may be obtained, for example, from a patient; that is, a living person, male or female, presenting oneself in a clinical setting for diagnosis, prognosis, or treatment of a disease or condition.

The present invention also contemplates kits for a DHA and/or EPA quantitation assay. A kit for a DHA and/or EPA quantitation assay may include a kit comprising the compositions provided herein. For example, a kit may include packaging material and measured amounts of packaged reagents, including an isotopically labeled internal standard, in amounts sufficient for at least one assay. Typically, the kits will also include instructions recorded in a tangible form (e.g., contained on paper or an electronic medium) for using the packaged reagents for use in a DHA and/or EPA quantitation assay.

Calibration and QC pools for use in embodiments of the present invention are preferably prepared using a matrix similar to the intended sample matrix.

Sample Preparation for Mass Spectrometric Analysis

In preparation for mass spectrometric analysis, free fatty acids (including DHA and/or EPA) in the sample may be enriched relative to their ester counterparts by hydrolysis of fatty acid esters. Hydrolysis may be accomplished by any technique known in the art. In some embodiments, fatty acid esters in the sample are hydrolyzed by contacting the sample with an acid, such as hydrochloric acid (HCl), and incubating at an elevated temperature, such as about 105° C. to about 115° C. The incubation period may vary depending on the amount of sample and concentration of acid used. Certain embodiments described herein utilize an incubation period of about 90 minutes to hydrolyze 200 µL of sample, diluted with 100 µL of internal standard, with 200 µL of 5 M HCl.

Additionally, DHA and/or EPA may be enriched relative to one or more other components in the sample (e.g. protein) by various methods known in the art, including for example any combination of liquid chromatography, filtration, centrifugation, thin layer chromatography (TLC), electrophoresis including capillary electrophoresis, affinity separations including immunoaffinity separations, extraction methods including ethyl acetate or methanol extraction, and the use of chaotropic agents or any combination of the above or the like. If both hydrolysis and purification steps are used, purification is preferably conducted after hydrolysis.

Protein precipitation is one method of preparing a test sample, especially a biological test sample, such as serum or plasma. Protein purification methods are well known in the art, for example, Polson et al., *Journal of Chromatography B* 2003, 785:263-275, describes protein precipitation techniques suitable for use in methods of the present invention. Protein precipitation may be used to remove most of the protein from the sample leaving vitamin D in the supernatant. The samples may be centrifuged to separate the liquid supernatant from the precipitated proteins; alternatively the samples may be filtered to remove precipitated proteins. The resultant supernatant or filtrate may then be applied directly to mass spectrometry analysis; or alternatively to liquid chromatography and subsequent mass spectrometry analysis. In certain embodiments, samples, such as plasma or serum, may be purified by a hybrid protein precipitation/liquid-liquid extraction method. In these embodiments, a sample is mixed with methanol, ethyl acetate, and water, and the resulting mixture is vortexed and centrifuged. The resulting supernatant is removed, dried to completion and reconstituted in a suitable solvent. In certain embodiments described herein, the solvent used to reconstitute the dried supernatant is ethanol.

Another method of sample purification that may be used prior to mass spectrometry is liquid chromatography (LC). Certain methods of liquid chromatography, including HPLC, rely on relatively slow, laminar flow technology. Traditional HPLC analysis relies on column packing in which laminar flow of the sample through the column is the basis for separation of the analyte of interest from the sample. The skilled artisan will understand that separation in such columns is a diffusional process and may select LC, including HPLC, instruments and columns that are suitable for use with DHA and/or EPA. The chromatographic column typically includes a medium (i.e., a packing material) to facilitate separation of chemical moieties (i.e., fractionation). The medium may include minute particles, or may include a monolithic material with porous channels. A surface of the medium typically includes a bonded surface that interacts with the various chemical moieties to facilitate separation of the chemical moieties. One suitable bonded surface is a hydrophobic bonded surface such as an alkyl bonded, cyano bonded surface, or highly pure silica surface. Alkyl bonded surfaces may include C-4, C-8, C-12, or C-18 bonded alkyl groups. In preferred embodiments, the column is a C-18 alkyl bonded column (such as a BDS Hypersil C18 column from Thermo Scientific). The chromatographic column includes an inlet port for receiving a sample and an outlet port for discharging an effluent that includes the fractionated sample. The sample may be supplied to the inlet port directly, or from an extraction column, such as an on-line SPE cartridge or a TFLC extraction column.

In one embodiment, the sample may be applied to the LC column at the inlet port, eluted with a solvent or solvent mixture, and discharged at the outlet port. Different solvent modes may be selected for eluting the analyte(s) of interest. For example, liquid chromatography may be performed using a gradient mode, an isocratic mode, or a polytyptic (i.e. mixed) mode. During chromatography, the separation of materials is effected by variables such as choice of eluent (also known as a "mobile phase"), elution mode, gradient conditions, temperature, etc.

In certain embodiments, an analyte may be purified by applying a sample to a column under conditions where the analyte of interest is reversibly retained by the column packing material, while one or more other materials are not retained. In these embodiments, a first mobile phase condition may be employed where the analyte of interest is retained by the column, and a second mobile phase condition may subsequently be employed to remove retained material from the column, once the non-retained materials are washed through. Alternatively, an analyte may be purified by applying a sample to a column under mobile phase conditions where the analyte of interest elutes at a differential rate in comparison to one or more other materials. Such procedures may enrich the amount of one or more analytes of interest relative to one or more other components of the sample.

In one preferred embodiment, HPLC is conducted with an alkyl bonded analytical column chromatographic system. In certain preferred embodiments, a C-18 alkyl bonded column (such as a BDS Hypersil C18 column from Thermo Scientific) is used. In certain embodiments, HPLC is performed using 20 mM ammonium acetate as mobile phase A and 100% acetonitrile as mobile phase B.

By careful selection of valves and connector plumbing, two or more chromatography columns may be connected as needed such that material is passed from one to the next without the need for any manual steps. In preferred embodiments, the selection of valves and plumbing is controlled by a computer pre-programmed to perform the necessary steps. Most preferably, the chromatography system is also connected in such an on-line fashion to the detector system, e.g., an MS system. Thus, an operator may place a tray of samples in an autosampler, and the remaining operations are performed under computer control, resulting in purification and analysis of all samples selected.

In some embodiments, an extraction column may be used for purification of DHA and/or EPA prior to mass spectrometry. In such embodiments, samples may be extracted using an extraction column which captures the analyte, then eluted and chromatographed on a second extraction column or on an analytical HPLC column prior to ionization. For example, sample extraction with a TFLC extraction column may be accomplished with a large particle size (50 µm) packed column. Sample eluted off of this column may then be transferred to an HPLC analytical column for further purification prior to mass spectrometry. Because the steps involved in these chromatography procedures may be linked in an automated fashion, the requirement for operator involvement during the purification of the analyte can be minimized. This feature may result in savings of time and costs, and eliminate the opportunity for operator error.

In some embodiments, purification of DHA and/or EPA is accomplished with liquid-liquid extraction. Liquid/liquid extraction may be accomplished by adding a suitable quantity of an organic solvent, such as 10% ethyl acetate in hexane, to the sample. This mixture is then vortexed and chilled, and the organic layer is decanted off for further analysis. In some embodiments, DHA and/or EPA in the sample may be purified by liquid/liquid extraction followed by liquid chromatography prior to mass spectrometric analysis.

Detection and Quantitation by Mass Spectrometry

Mass spectrometry is performed using a mass spectrometer, which includes an ionization source for ionizing the fractionated sample and creating charged molecules for further analysis. For example, ionization of the sample may be performed by electron ionization, chemical ionization, electrospray ionization (ESI), photon ionization, atmospheric pressure chemical ionization (APCI), photoionization, atmospheric pressure photoionization (APPI), laser diode thermal desorption (LDTD), fast atom bombardment (FAB), liquid secondary ionization (LSI), matrix assisted laser desorption ionization (MALDI), field ionization, field desorption, thermospray/plasmaspray ionization, surface enhanced laser desorption ionization (SELDI), inductively coupled plasma (ICP) and particle beam ionization. In preferred embodiments, DHA and/or EPA in the sample are ionized by APCI.

Mass spectrometric techniques may be conducted in positive or negative ionization mode. In preferred embodiments, DHA and/or EPA are ionized by APCI in negative ionization mode.

In mass spectrometry techniques generally, after the sample has been ionized, the positively or negatively charged ions created thereby may be analyzed to determine a mass-to-charge ratio. Suitable analyzers for determining mass-to-charge ratios include quadrupole analyzers, ion traps analyzers, and time-of-flight analyzers. Exemplary ion trap methods are described in Bartolucci, et al., *Rapid Commun. Mass Spectrom.* 2000, 14:967-73.

Ions in a MS system may be detected using several detection modes. For example, selected ions may be detected, i.e. using a selective ion monitoring mode (SIM), or alternatively, mass transitions resulting from collision induced dissociation or neutral loss may be monitored, e.g., multiple reaction monitoring (MRM) or selected reaction monitoring (SRM). Preferably, the mass-to-charge ratio is determined using a quadrupole analyzer. For example, in a "quadrupole" or "quadrupole ion trap" instrument, ions in an oscillating radio frequency field experience a force proportional to the DC potential applied between electrodes, the amplitude of the RF signal, and the mass/charge ratio. The voltage and amplitude may be selected so that only ions having a particular mass/charge ratio travel the length of the quadrupole, while all other ions are deflected. Thus, quadrupole instruments may act as both a "mass filter" and as a "mass detector" for the ions injected into the instrument.

One may enhance the resolution of the MS technique by employing "tandem mass spectrometry," or "MS/MS". In this technique, a precursor ion (also called a parent ion) generated from a molecule of interest can be filtered in an MS instrument, and the precursor ion subsequently fragmented to yield one or more fragment ions (also called daughter ions or product ions) that are then analyzed in a second MS procedure. By careful selection of precursor ions, only ions produced by certain analytes are passed to the fragmentation chamber, where collisions with atoms of an inert gas produce the fragment ions. Because both the precursor and fragment ions are produced in a reproducible fashion under a given set of ionization/fragmentation conditions, the MS/MS technique may provide an extremely powerful analytical tool. For example, the combination of filtration/fragmentation may be used to eliminate interfering substances, and may be particularly useful in complex samples, such as biological samples.

Alternate modes of operating a tandem mass spectrometric instrument include product ion scanning and precursor ion scanning. For a description of these modes of operation, see, e.g., E. Michael Thurman, et al., Chromatographic-Mass Spectrometric Food Analysis for Trace Determination of Pesticide Residues, Chapter 8 (Amadeo R. Fernandez-Alba, ed., Elsevier 2005) (387).

The results of an analyte assay may be related to the amount of the analyte in the original sample by numerous methods known in the art. For example, given that sampling and analysis parameters are carefully controlled, the relative abundance of a given ion may be compared to a table that converts that relative abundance to an absolute amount of the original molecule. Alternatively, external standards may be run with the samples, and a standard curve constructed based on ions generated from those standards. Using such a standard curve, the relative abundance of a given ion may be converted into an absolute amount of the original molecule. In certain preferred embodiments, an internal standard is used to generate a standard curve for calculating the quantity of DHA and/or EPA in the sample. Methods of generating and using such standard curves are well known in the art and one of ordinary skill is capable of selecting an appropriate internal standard. For example, in some embodiments one or more isotopically labeled DHA and/or EPA (e.g., DHA-$^2H_5$ and EPA-$^2H_5$) may be used as internal standards. Numerous other methods for relating the amount of an ion to the amount of the original molecule will be well known to those of ordinary skill in the art.

One or more steps of the methods may be performed using automated machines. In certain embodiments, one or more purification steps are performed on-line, and more preferably all of the purification and mass spectrometry steps may be performed in an on-line fashion.

In certain embodiments, such as MS/MS, where precursor ions are isolated for further fragmentation, collision activated dissociation (CAD) is often used to generate fragment ions for further detection. In CAD, precursor ions gain energy through collisions with an inert gas, and subsequently fragment by a process referred to as "unimolecular decomposition." Sufficient energy must be deposited in the precursor ion so that certain bonds within the ion can be broken due to increased vibrational energy.

In some preferred embodiments, DHA and/or EPA in a sample are detected and/or quantitated using MS as follows. The samples are first purified by liquid-liquid extraction. Then, the purified sample is subjected to liquid chromatography, preferably on an analytical column (such as a HPLC column) and the flow of eluted DHA and/or EPA from the chromatographic column is directed to the ionization source of an MS analyzer. DHA and/or EPA from the chromatographic column are ionized via APCI in negative ionization mode. The generated ions pass through the orifice of the instrument and enter a quadrupole. The quadrupole acts as a mass filter, allowing selection of ions (i.e., selection of "precursor" and "fragment" ions in Q1 and Q3, respectively) based on their mass to charge ratio (m/z). The quadrupole selects for ions with the mass to charge ratios of DHA and/or EPA ions of interest. Ions with the correct mass/charge ratios are allowed to pass the quadrupole and collide with the detector.

As ions collide with the detector they produce a pulse of electrons that are converted to a digital signal. The acquired data is relayed to a computer, which plots counts of the ions collected versus time. The areas under the peaks corresponding to particular ions, or the amplitude of such peaks, may be measured and correlated to the amount of the analyte of interest. In certain embodiments, the area under the curves, or amplitude of the peaks, for DHA and/or EPA ions are measured to determine the amount of DHA and/or EPA in the original sample. As described above, the relative abundance of a given ion may be converted into an absolute amount of the original analyte using calibration standard curves based on peaks of one or more ions of an internal molecular standard.

The following Examples serve to illustrate the invention. These Examples are in no way intended to limit the scope of the methods. In particular, the Examples demonstrate quantitation of DHA and/or EPA by mass spectrometry, and the use of DHA-$^2$H$_5$ and EPA-$^2$H$_5$ as internal standards. The use of DHA-$^2$H$_5$ and EPA-$^2$H$_5$ as internal standards are not meant to be limiting in any way. Any appropriate chemical species, easily determined by one in the art, may be used as an internal standard.

EXAMPLES

Example 1

Reagent Preparation

Three control solutions (at low, medium, and high DHA and EPA concentrations) were prepared for use in the following Examples. The control solutions were prepared by spiking DHA and EPA into Biocel serum samples to achieve final concentrations of 45 µmol/L DHA and 25 µmol/L EPA for the low level control, 120 µmol/L DHA and 65 µmol/L EPA for the mid level control, and 400 µmol/L DHA and 125 µmol/L EPA for the high level control.

A standard stock solution was similarly prepared by spiking DHA and EPA into Biocel serum samples to target concentrations of 600 µmol/L DHA and 300 µmol/L EPA. A series of 1:2 dilutions of the standard stock solution was prepared for use below in generation of a calibration curve (discussed in Example 4).

An internal standard solution was prepared by diluting both DHA-$^2$H$_5$ and EPA-$^2$H$_5$ in the same ethyl alcohol solution to concentrations of about 150 µmol/L and 50 µmol/L, respectfully.

Example 2

Hydrolysis of Fatty Acid Esters and Liquid-Liquid Extraction

The following hydrolysis and liquid-liquid extraction techniques were conducted on controls, standards, and patient serum samples to prepare samples for mass spectrometric analysis. Plasma samples were also tested with similar results (not shown).

First, 100 µL of the DHA-$^2$H$_5$ and EPA-$^2$H$_5$ internal standard mixture described above was mixed with 200 µL aliquots of each standard, control, and patient sample. 200 µL of 5 M HCL was added to each mixture, and the resulting mixtures vortexed for about 10 seconds. The acidified mixtures were then placed in an oven and incubated at about 105° C.-115° C. for about 90 minutes.

After incubation was complete, the mixtures were cooled in a 2° C.-8° C. refrigerator for 5-10 minutes. 3.5 mL of 10% ethyl acetate in hexane was added to each of the cooled samples; the resulting mixtures vortexed for 4 minutes and centrifuged at about 3000 rpm for about 5 minutes. After centrifugation, the samples were placed in a methanol/dry ice bath for about 5 minutes to freeze the aqueous later. The organic layer was then decanted off, dried to completion under a flowing nitrogen gas manifold, and reconstituted in 150 µL of ethanol.

The resulting samples were transferred to HPLC vials and placed in an autosampler for analysis.

Example 3

Purification of DHA and EPA with Liquid Chromatography

Sample injection was performed with an Agilent Technologies G1367B Autosampler.

The autosampler system automatically injected an aliquot of the above prepared reconstituted samples into a Thermo Scientific BDS Hypersil C18 HPLC column (3 µm particle size, 100×2.1 mm, from Thermo Scientific). An HPLC gradient was applied to the analytical column, to separate DHA and EPA from other components in the sample. Mobile phase A was 20 mM ammonium acetate and mobile phase B was 100% acetonitrile. The HPLC gradient started with a 54% solvent A which was ramped to 82% in approximately 2.5 minutes, and held for approximately 30 seconds, before being ramped back down to 54% over the next 30 seconds. Column flow rate during solvent application was about 0.75 mL/min. DHA and EPA were observed to elute off the column at approximately 1.40 minutes into the gradient profile.

Example 4

Detection and Quantitation of DHA and EPA by MS

MS was performed on the above eluted samples using an Agilent 6130 Single Quadrupole Mass Spectrometer. Liquid solvent/analyte exiting the analytical column flowed to the ionization interface of the MS/MS analyzer. The solvent/analyte mixture was converted to vapor in the tubing of the interface. Analytes in the nebulized solvent were ionized by APCI.

Ions passed to the quadrupole mass selector (Q1), which selected DHA and EPA ions with mass-to-charge ratios of 327.2±0.5 m/z and 301.2±0.5 m/z, respectively. The selected DHA and EPA ions then traveled to a detector for counting. Mass spectrometer settings used for this Example are shown in Table 1. Simultaneously, the same process using isotope dilution mass spectrometry was carried out with internal standards, DHA-$^2$H$_5$ and EPA-$^2$H$_5$. The masses monitored for detection and quantitation during validation on negative polarity are shown in Table 2.

TABLE 1

Mass Spectrometer Settings for Detection of DHA, EPA, DHA-$^2$H$_5$ (internal standard), and EPA-$^2$H$_5$ (internal standard) (Negative Ionization)
Mass Spectrometric Instrument Settings

| | |
|---|---|
| Gas Temperature | 345° C. |
| Vaporizer Temperature | 245° C. |
| Drying Gas Flow | 10.0 L/min |
| Nebulizer Pressure | 50 psig |
| Vcap (positive) | 4000 V |
| Vcap (negative) | 2400 V |
| Vcharge (positive) | 2000 V |
| Vcharge (negative) | 1000 V |
| Corona (positive) | 5.0 µA |
| Corona (negative) | 40 µA |

TABLE 2

Mass-to-Charge ratios monitored for DHA, EPA, DHA-$^2$H$_5$ (internal standard), and EPA-$^2$H$_5$ (internal standard) (Negative Ionization)

| Analyte | Ion (m/z) |
|---|---|
| DHA | 327.2 ± 0.5 |
| EPA | 301.2 ± 0.5 |
| DHA-$^2$H$_5$ | 332.1 ± 0.5 |
| EPA-$^2$H$_5$ | 306.2 ± 0.5 |

Figure 2:
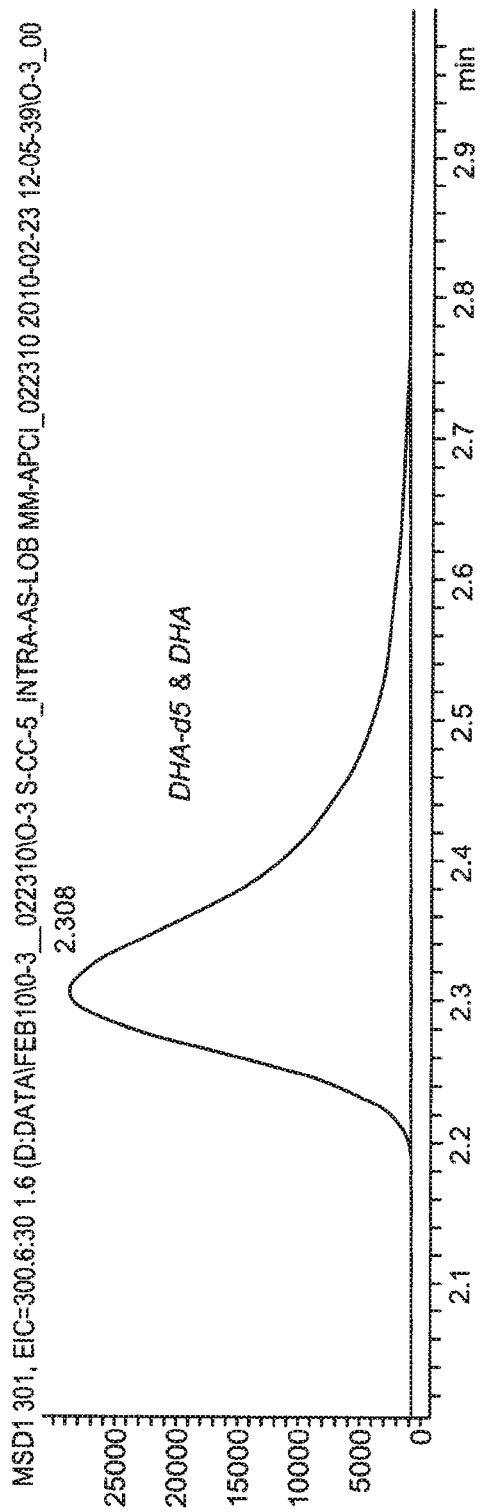
FIG. 2 shows an exemplary chromatogram for DHA and DHA-$^2$H$_5$ (internal standard). Details are discussed in Example 4.

Exemplary chromatograms for EPA/EPA-$^2$H$_5$ (internal standard) and DHA/DHA-$^2$H$_5$ (internal standard) are shown in FIGS. 1 and 2, respectively.

Figure 3:
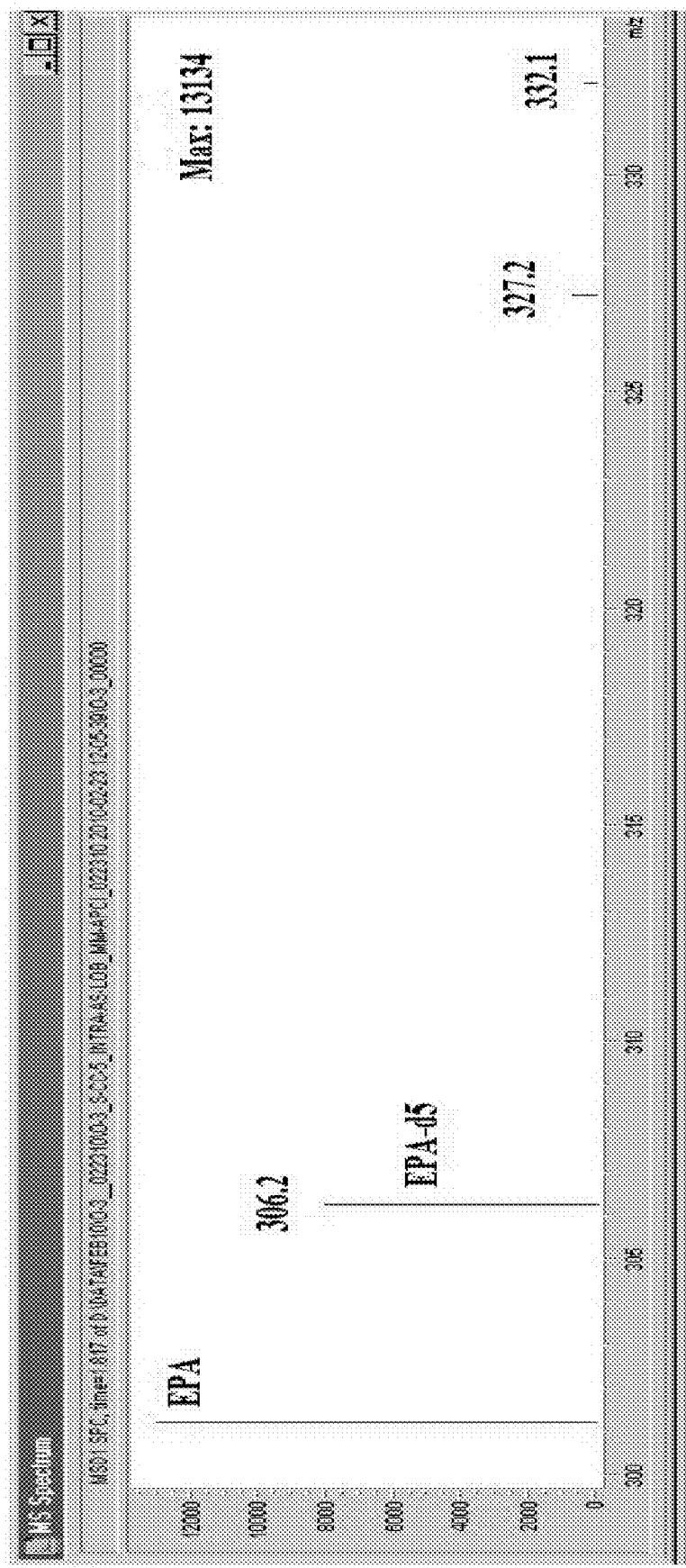
FIG. 3 shows exemplary spectra demonstrating detection of EPA and EPA-$^2$H$_5$ (internal standard). Details are discussed in Example 4.
Figure 4:
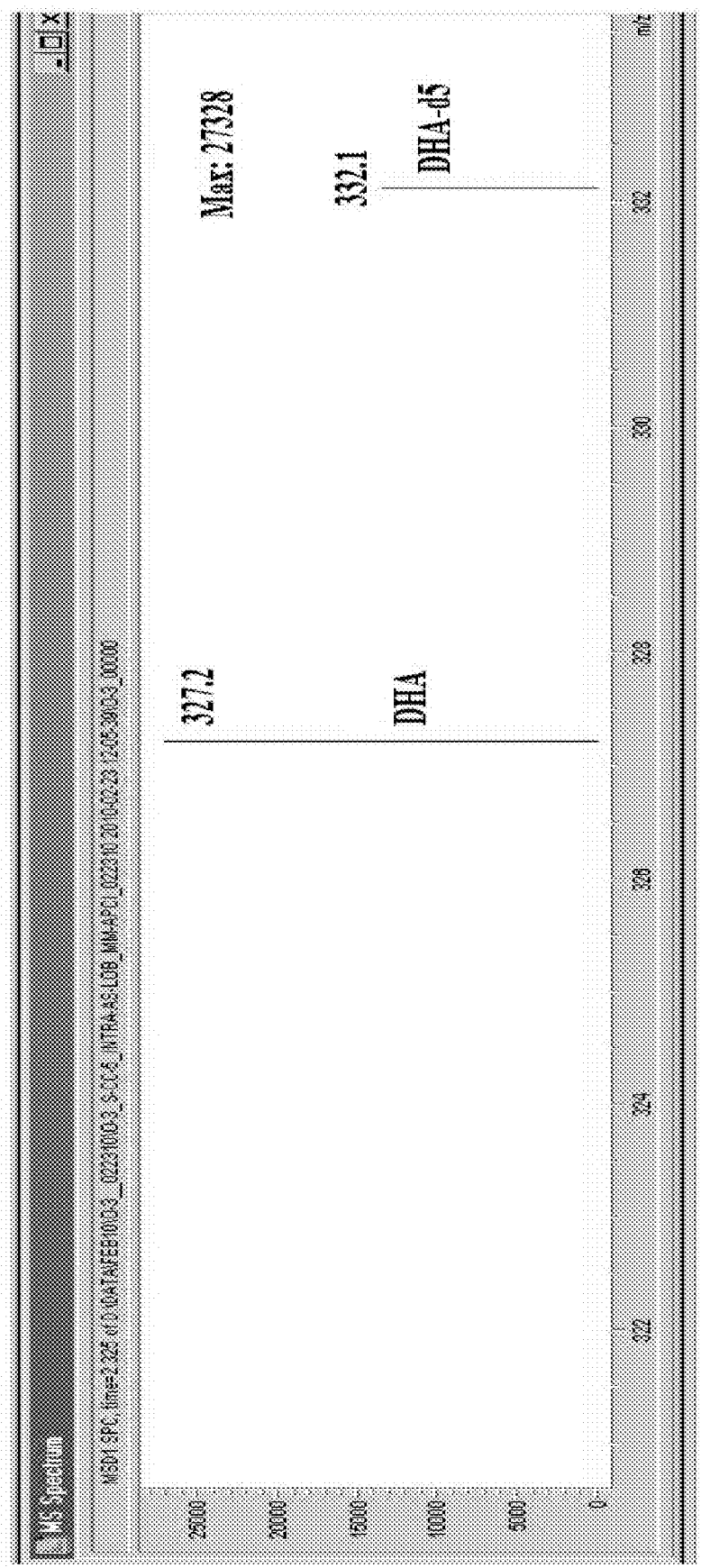
FIG. 4 shows exemplary spectra demonstrating detection of DHA and DHA-$^2$H$_5$ (internal standard). Details are discussed in Example 4.

Exemplary spectra from the mass spectrometric analysis of EPA/EPA-$^2$H$_5$ (internal standard) and DHA/DHA-$^2$H$_5$ (internal standard) generated as described above are shown in FIGS. 3 and 4, respectively. The spectra were collected by scanning Q1 across a m/z range of about 300 to 333 for EPA, and about 321 to 333 for DHA.

Figure 5:
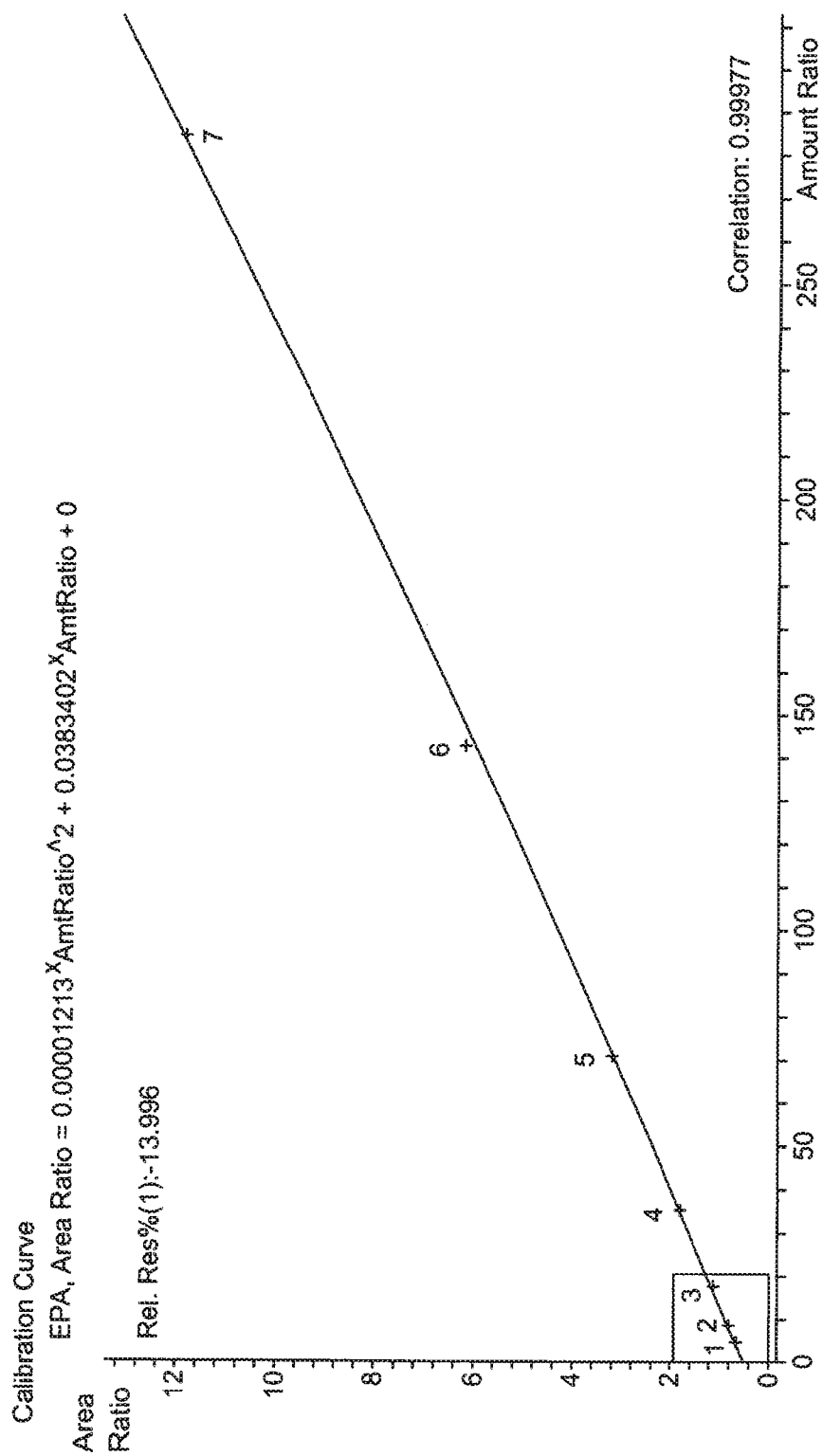
FIGS. 5 and 6 show exemplary calibration curves generated for DHA and EPA, respectively, from serially diluted serum standards. Details are described in Example 4.
Figure 6:
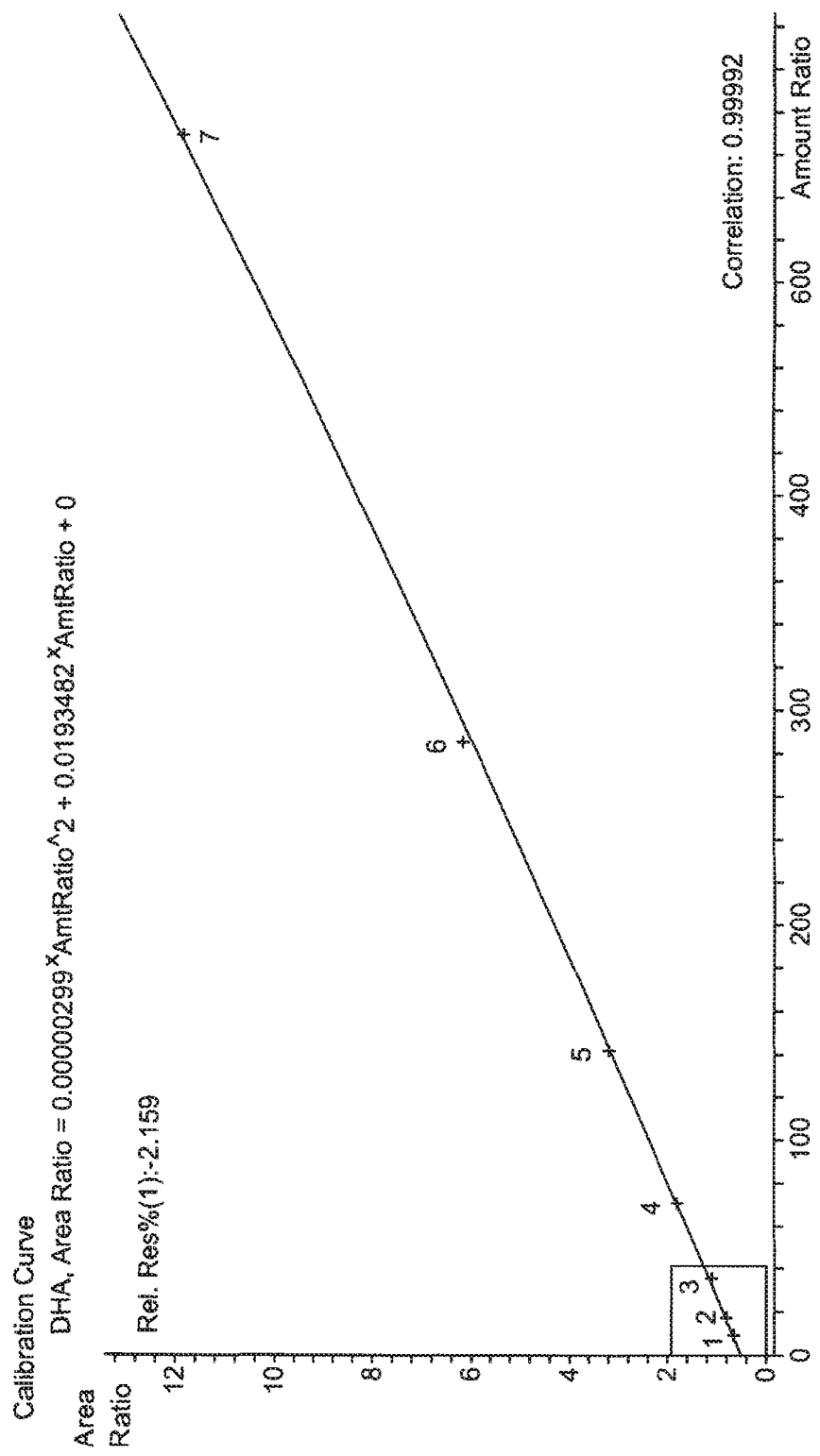

Calibration curves were prepared for the quantitation of DHA and EPA in serum by analysis of standards at about 600 µmol/L DHA and 300 µmol/L EPA (std. 1), 300 µmol/L DHA and 150 µmol/L EPA (std. 2), 150 µmol/L DHA and 75 µmol/L EPA (std. 3), 75 µmol/L DHA and 37.5 µmol/L EPA (std. 4), 37.5 µmol/L DHA and 18.8 µmol/L EPA (std. 5), 18.8 µmol/L DHA and 9.4 µmol/L EPA (std. 6), and 9.4 µmol/L DHA and 4.7 µmol/L EPA (std. 7). Exemplary calibration curves for the determination of EPA and DHA in serum specimens are shown in FIGS. 5 and 6, respectively. Analysis of the data generated for these standards demonstrates that the assay exhibits linear response for DHA in the concentration range of about 0.912 µmol/L to 600 µmol/L (correlation of about 0.99992), and for EPA in the concentration range of about 2.278 µmol/L to 300 µmol/L (correlation of about 0.99977).

Example 5

Analytical Precision for MS Determination of DHA and EPA

Intra-assay precision studies for DHA were conducted by analyzing multiple aliquots of the three control solutions described in Example 1 according to the analytical techniques described in Examples 2-4. Statistical analysis of the results of these studies gave CVs of 4.9%, 3.6%, and 2.9%, for the low, mid, and high concentration levels, respectively. For all three controls, the observed standard deviation (n=24 samples) was less than one quarter of the total allowable error. Additionally, pooled within-run CVs from the inter-assay precision study (n=25 samples) were 3.6%, 3.2%, and 2.6%, respectively. Again, all observed within-run standard deviations were less than one quarter of the total allowable error.

Intra-assay precision studies for EPA were conducted by analyzing multiple aliquots of the three control solutions described in Example 1 according to the analytical techniques described in Examples 2-4. Statistical analysis of the results of these studies gave CVs of 3.0%, 1.1%, and 2.0%, for the low, mid, and high concentration levels, respectively. For all three controls, the observed standard deviation (n=24 samples) was less than one quarter of the total allowable error. Additionally, pooled within-run CVs from the inter-assay precision study (n=25 samples) were 2.9%, 3.5%, and 2.6%, respectively. Again, all observed within-run standard deviations were less than one quarter of the total allowable error.

Inter-assay precision studies for DHA were conducted by analyzing multiple aliquots of the three control solutions described in Example 1 according to the analytical techniques described in Examples 2-4. Statistical analysis of the results of these studies gave CVs of 5.7%, 4.8%, and 3.7%, for the low, mid, and high concentration levels, respectively. For all three controls, the observed standard deviation (n=24 samples) was less than one half of the total allowable error. Additionally, pooled within-run CVs from the inter-assay precision study (n=25 samples) were 3.92%, 4.64%, and 6.06%, respectively.

Inter-assay precision studies for EPA were conducted by analyzing multiple aliquots of the three control solutions described in Example 1 according to the analytical techniques described in Examples 2-4. Statistical analysis of the results of these studies gave CVs of 4.49%, 4.14%, and 4.44%, for the low, mid, and high concentration levels, respectively. For all three controls, the observed standard deviation (n=24 samples) was less than one half of the total allowable error. Additionally, pooled within-run CVs from the inter-assay precision study (n=25 samples) were 4.90%, 5.31%, and 4.96%, respectively.

Example 6

Analytical Sensitivity: Limit of Blank (LOB), Lower Limit of Quantitation (LLOQ), and Limit of Detection (LOD)

The limit of blank (LOB) is defined as the mean value of analysis of several blank samples plus two standard deviations. The LOB was determined for DHA to be 0.236 µmol/L, and for EPA to be 0.654 µmol/L. Data generated for the determination of LOB of DHA and EPA are shown in Table 4.

The lower limit of quantitation (LLOQ) is the point where measurements become quantitatively meaningful. The analyte response at this LLOQ is identifiable, discrete and reproducible with a standard deviation of less than TEa/3. The LLOQ was determined by analyzing the low, medium, and high concentration controls prepared in Example 1. Five replicates of each control were analyzed five times. The LLOQ was determined for DHA to be 0.912 µmol/L, and for EPA to be 2.278 µmol/L. Data generated for the determination of LLOQ of DHA and EPA are shown in Table 3.

TABLE 3

Determination of Lower Limit of Quantitation of DHA and EPA

| | DHA | | | | EPA | | |
|---|---|---|---|---|---|---|---|
| | Controls (μmol/L) | | | | Controls (μmol/L) | | |
| Run | Low | Medium | High | Run | Low | Medium | High |
| 1 | 0.972 | 2.193 | 4.334 | 1 | 0.534 | 1.193 | 2.329 |
| | 0.933 | 2.192 | 4.455 | | 0.488 | 1.207 | 2.204 |
| | 0.907 | 2.202 | 4.225 | | 0.616 | 1.167 | 2.255 |
| | 0.942 | 2.175 | 4.310 | | 0.558 | 1.169 | 2.301 |
| | 0.941 | 2.173 | 4.241 | | 0.504 | 1.134 | 2.252 |
| 2 | 0.935 | 2.075 | 4.174 | 2 | 0.555 | 1.175 | 2.168 |
| | 0.920 | 2.072 | 4.068 | | 0.595 | 1.155 | 2.223 |
| | 0.937 | 2.044 | 4.185 | | 0.506 | 1.142 | 2.283 |
| | 0.917 | 2.070 | 4.480 | | 0.552 | 1.110 | 2.261 |
| | 0.908 | 1.976 | 4.145 | | 0.515 | 1.123 | 2.250 |
| 3 | 0.943 | 2.430 | 4.640 | 3 | 0.579 | 1.347 | 2.498 |
| | 0.883 | 2.399 | 4.571 | | 0.403 | 1.384 | 2.440 |
| | 0.982 | 2.375 | 4.537 | | 0.530 | 1.370 | 2.518 |
| | 0.923 | 2.376 | 4.565 | | 0.533 | 1.321 | 2.476 |
| | 0.956 | 2.505 | 4.665 | | 0.398 | 1.407 | 2.556 |
| 4 | 0.905 | 1.964 | 4.572 | 4 | 0.546 | 0.979 | 2.199 |
| | 0.853 | 1.978 | 4.571 | | 0.370 | 1.006 | 2.272 |
| | 0.797 | 1.992 | 4.390 | | 0.279 | 0.944 | 2.246 |
| | 0.877 | 1.977 | 4.445 | | 0.274 | 0.992 | 2.121 |
| | 0.893 | 1.939 | 4.530 | | 0.226 | 0.969 | 2.250 |
| 5 | 0.923 | 2.101 | 4.442 | 5 | 0.466 | 1.005 | 2.103 |
| | 0.878 | 2.094 | 4.414 | | 0.484 | 0.996 | 2.123 |
| | 0.885 | 2.086 | 4.689 | | 0.388 | 0.991 | 2.123 |
| | 0.888 | 2.062 | 4.449 | | 0.394 | 1.072 | 2.267 |
| | 0.902 | 2.129 | 4.471 | | 0.412 | 0.975 | 2.232 |
| Count | 25 | 25 | 25 | Count | 25 | 25 | 25 |
| Mean | 0.912 | 2.143 | 4.423 | Mean | 0.468 | 1.133 | 2.278 |
| SD | 0.039 | 0.160 | 0.172 | SD | 0.105 | 0.144 | 0.127 |
| TEa/3 | 0.068 | 0.161 | 0.332 | TEa/3 | 0.034 | 0.083 | 0.167 |
| LOB | | 0.236 | | LOB | | | 0.654 |
| LOQ | | 0.912 | | LOQ | | | 2.278 |

The limit of detection (LOD) is the point where a measured value is larger than the uncertainty associated with it and is defined arbitrarily as four standard deviations (SD) from the means signal from zero concentration. A blank was run in 20 replicates and the resulting area ratios were statistically analyzed. From this analysis, the LOD for DHA and EPA were determined to be about 0.258 μmol/L and 0.67 μmol/L, respectively. Data collected to determine LOD for each analyte is shown in Table 6.

TABLE 4

Determination of Limit of Detection of DHA and EPA

| Replicate # | DHA (Response Ratio) (μmol/L) | EPA (Response Ratio) (μmol/L) |
|---|---|---|
| 1 | 0.205 | 0.633 |
| 2 | 0.228 | 0.636 |
| 3 | 0.221 | 0.657 |
| 4 | 0.238 | 0.632 |
| 5 | 0.193 | 0.630 |
| 6 | 0.205 | 0.634 |
| 7 | 0.210 | 0.643 |
| 8 | 0.215 | 0.633 |
| 9 | 0.222 | 0.633 |
| 10 | 0.218 | 0.640 |
| 11 | 0.220 | 0.637 |
| 12 | 0.208 | 0.654 |
| 13 | 0.197 | 0.635 |
| 14 | 0.224 | 0.629 |
| 15 | 0.215 | 0.639 |
| 16 | 0.207 | 0.628 |
| 17 | 0.205 | 0.626 |

TABLE 4-continued

Determination of Limit of Detection of DHA and EPA

| Replicate # | DHA (Response Ratio) (μmol/L) | EPA (Response Ratio) (μmol/L) |
|---|---|---|
| 18 | 0.209 | 0.649 |
| 19 | 0.228 | 0.638 |
| 20 | 0.210 | 0.633 |
| Mean | 0.214 | 0.637 |
| SD | 0.011 | 0.008 |
| LOB | 0.236 μmol/L | 0.654 μmol/L |
| LOD | 0.258 μmol/L | 0.670 μmol/L |

Example 7

Analyte Measurement Range (AMR)

A sample with a low DHA value (mean 60.42 μmol/L) and a sample with a high DHA value (mean 600.14 μmol/L) were mixed in various proportions and analyzed according to the method outlined in the Examples above. The observed results were compared to the expected (calculated) results. For all admixtures, the difference between the observed mean DHA value and the expected (calculated) value was less than TEa/4. Results of these studies are presented in Table 5.

TABLE 5

Comparison of Observed and Expected Values for Various Levels of DHA in Mixed Serum Samples

| Sample Mix (% High/% Low) | Mean Observed (µmol/L) | Expected (Calculated) (µmol/L) | TEa/4 | Difference |
|---|---|---|---|---|
| 0/100 | 60.42 | 60.42 | 3.4 | 0.00 |
| 25/75 | 188.66 | 195.35 | 10.61 | −6.75 |
| 50/50 | 336.46 | 330.28 | 18.93 | 6.18 |
| 75/25 | 456.35 | 465.21 | 25.67 | −8.86 |
| 100/0 | 600.14 | 600.14 | 33.76 | 0.00 |

A sample with a low EPA value (mean 10.92 µmol/L) and a sample with a high EPA value (mean 282.52 µmol/L) were mixed in various proportions and analyzed according to the method outlined in the Examples above. The observed results were compared to the (calculated) expected results. For all admixtures, the difference between the observed mean EPA value and the expected (calculated) value was less than TEa/4. Results of these studies are presented in Table 6.

TABLE 6

Comparison of Observed and Expected Values for Various Levels of EPA in Mixed Serum Samples

| Sample Mix (% High/% Low) | Mean Observed (µmol/L) | Expected (Calculated) (µmol/L) | TEa/4 | Difference |
|---|---|---|---|---|
| 0/100 | 10.92 | 10.92 | 0.60 | 0.00 |
| 25/75 | 81.02 | 78.82 | 4.46 | 2.19 |
| 50/50 | 151.73 | 146.72 | 8.34 | 5.00 |
| 75/25 | 218.75 | 214.62 | 12.03 | 4.13 |
| 100/0 | 282.52 | 282.52 | 15.54 | 0.00 |

Example 8

Recovery Studies for DHA and EPA

Six serum samples with low baseline DHA and EPA levels were selected for analysis according to the method described in the above Examples for recovery studies. A known amount of standard (comprising known amounts of DHA and EPA) was added to each sample to establish a target level to assess recoveries. Each spiked sample was tested in quadruplicate. The difference between the mean of the four measurements and its target value were calculated. The results for DHA and EPA are summarized in Tables 7-8, respectively:

TABLE 7

Recovery of DHA in Serum Samples

| Sample | Target Value (µmol/L) | Mean Observed (µmol/L) | TEa/4 | Difference |
|---|---|---|---|---|
| 1 | 155.54 | 141.14 | 8.75 | 14.4 |
| 2 | 167.57 | 155.79 | 9.43 | 11.78 |
| 3 | 233.74 | 221.17 | 13.15 | 12.57 |
| 4 | 343.59 | 333.46 | 19.33 | 10.13 |
| 5 | 72.50 | 62.68 | 4.08 | 9.82 |
| 6 | 586.33 | 585.41 | 32.98 | 0.92 |

For analysis of DHA, the difference between the target amount and the observed amount was less than TEa/4 for samples 3, 4, and 6. However, the difference between the observed and targeted values for all samples was not large enough to be clinically significantly.

TABLE 8

Recovery of EPA in Serum Samples

| Sample | Target Value (µmol/L) | Mean Observed (µmol/L) | TEa/4 | Difference |
|---|---|---|---|---|
| 1 | 35.84 | 33.38 | 1.97 | 2.46 |
| 2 | 48.51 | 47.23 | 2.67 | 1.28 |
| 3 | 124.02 | 125.09 | 6.82 | 1.07 |
| 4 | 249.98 | 253.26 | 13.75 | 3.28 |
| 5 | 11.63 | 10.26 | 0.64 | 1.37 |
| 6 | 527.08 | 530.96 | 28.99 | 3.88 |

For analysis of EPA, the difference between the target amount and the observed amount was less than TEa/4 for samples 3, 4, and 6. However, the difference between the observed and targeted values for all samples was not large enough to be clinically significantly.

Example 9

Interference Studies

Hemolysis Interference: The effects of hemolysis in the assay were evaluated by spiking various levels of washed red cells into the low and high DHA and EPA controls (described in Example 1) to mimic various degrees of hemolysis (low red, red, cherry red, dark red). All samples were analyzed in quadruplet for DHA and EPA. The results of these analyses are shown in Tables 9 and 10.

TABLE 9

Hemolysis Interference Studies for DHA

| Sample | Mean Baseline (µmol/L) | Mean Observed (µmol/L) | TEa/4 | Difference |
|---|---|---|---|---|
| DHA Low Control | | | | |
| Low Red | 40.26 | 42.26 | 2.26 | 2.00 |
| Red | 40.26 | 42.67 | 2.26 | 2.41 |
| Cherry Red | 40.26 | 46.78 | 2.26 | 6.52 |
| Dark Red | 40.26 | 52.22 | 2.26 | 11.96 |
| DHA High Control | | | | |
| Low Red | 347.76 | 346.96 | 19.56 | 0.80 |
| Red | 347.76 | 339.01 | 19.56 | 8.75 |
| Cherry Red | 347.76 | 353.76 | 19.56 | 6.00 |
| Dark Red | 347.76 | 360.40 | 19.56 | 12.64 |

TABLE 10

Hemolysis Interference Studies for EPA

| Sample | Mean Baseline (µmol/L) | Mean Observed (µmol/L) | TEa/4 | Difference |
|---|---|---|---|---|
| EPA Low Control | | | | |
| Low Red | 23.64 | 24.35 | 1.30 | 0.71 |
| Red | 23.64 | 24.68 | 1.30 | 1.04 |
| Cherry Red | 23.64 | 23.70 | 1.30 | 0.06 |
| Dark Red | 23.64 | 26.02 | 1.30 | 2.38 |
| EPA High Control | | | | |
| Low Red | 108.66 | 108.74 | 5.98 | 0.08 |
| Red | 108.66 | 109.98 | 5.98 | 1.32 |
| Cherry Red | 108.66 | 111.33 | 5.98 | 2.67 |
| Dark Red | 108.66 | 109.33 | 5.98 | 0.67 |

Although the high control data suggest that hemolysis has little or no effect on samples where the levels of DHA and EPA are high, the relatively large effect seen in samples with low DHA and EPA values prevents acceptability of hemolyzed samples.

Bilirubin Interference: The effects of bilirubin in the assay were evaluated by spiking various levels of bilirubin into the low level DHA and EPA control (described in Example 1) to mimic mildly (5 mg/dL bilirubin), moderately (10 mg/dL bilirubin), and grossly (40 mg/dL bilirubin) icteric samples. All samples were analyzed in quadruplet for DHA and EPA. The results of these analyses are shown in Tables 11 and 12.

TABLE 11

Bilirubin Interference Studies for DHA
DHA Low Control

| Sample | Mean Baseline (µmol/L) | Mean Observed (µmol/L) | TEa/4 | Difference |
|---|---|---|---|---|
| Mild | 82.10 | 84.94 | 4.61 | 2.93 |
| Moderate | 82.10 | 85.36 | 4.61 | 3.35 |
| Gross | 82.10 | 85.62 | 4.61 | 3.61 |

TABLE 12

Bilirubin Interference Studies for EPA
EPA Low Control

| Sample | Mean Baseline (µmol/L) | Mean Observed (µmol/L) | TEa/4 | Difference |
|---|---|---|---|---|
| Mild | 49.31 | 52.32 | 2.71 | 3.01 |
| Moderate | 49.31 | 51.91 | 2.71 | 2.60 |
| Gross | 49.31 | 51.48 | 2.71 | 2.17 |

For both DHA and EPA, the differences between the observed mean values and the expected value were greater than TEa/4 at all levels of icterus, except for EPA in the midly icteric sample. Thus, icteric samples are unacceptable for this assay.

Example 10

Development of Reference Intervals for DHA and EPA

Specimens were collected from 120 sources (60 female and 60 male) for DHA and 119 sources (60 female and 59 male) for EPA from apparently healthy, ambulatory, community dwelling, and non-medicated adults. Exclusion criteria for development of the reference range population were: no fish oil, DHA, or EPA dietary supplements, or patients that report a diet rich in seafood (i.e., greater than 1 serving per week).

The above specimens were analyzed for DHA and EPA according to the procedures outlined in Examples 1-3. The resulting data were neither age nor gender dependent, and were Gaussian, with logarithmic transformation. Reference ranges were defined as the logarithmic (transformed) mean±2 standard deviations. The reference range for DHA is about 48.98-250.03 µmol/L. The reference range for EPA is about 6.43-87.90 µmol/L.

The contents of the articles, patents, and patent applications, and all other documents and electronically available information mentioned or cited herein, are hereby incorporated by reference in their entirety to the same extent as if each individual publication was specifically and individually indicated to be incorporated by reference. Applicants reserve the right to physically incorporate into this application any and all materials and information from any such articles, patents, patent applications, or other physical and electronic documents.

The methods illustratively described herein may suitably be practiced in the absence of any element or elements, limitation or limitations, not specifically disclosed herein. Thus, for example, the terms "comprising", "including," "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof. It is recognized that various modifications are possible within the scope of the invention claimed. Thus, it should be understood that although the present invention has been specifically disclosed by preferred embodiments and optional features, modification and variation of the invention embodied therein herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the methods. This includes the generic description of the methods with a proviso or negative limitation removing any subject matter from the genus, regardless of whether or not the excised material is specifically recited herein.

Other embodiments are within the following claims. In addition, where features or aspects of the methods are described in terms of Markush groups, those skilled in the art will recognize that the invention is also thereby described in terms of any individual member or subgroup of members of the Markush group.

That which is claimed is:

1. A method for determining an amount of one or more omega-3 fatty acids in a sample by mass spectrometry, the method comprising:
   (i) ionizing said one or more omega-3 fatty acids from the sample to generate one or more omega-3 fatty acid ions detectable by mass spectrometry;
   (ii) determining an amount of said one or more omega-3 fatty acid ions and docosahexaenoic acid (DHA)-$^2H_5$ or eicosapentaenoic acid (EPA)-$^2H_5$ internal standard by single mass spectrometry; and
   (iii) correlating the amount of said one or more omega-3 fatty acid ions to the amount of one or more omega-3 fatty acids in the sample, wherein said one or more omega-3 fatty acids comprises docosahexaenoic acid (DHA) and/or eicosapentaenoic acid (EPA), wherein a lower limit of detection of the method for DHA is between about 1 µmol/L and 0.25 µmol/L and a lower limit of detection of the method for EPA is between about 1 µmol/L and 0.67 µmol/L.

2. The method of claim 1, wherein said ionizing comprises atmospheric pressure chemical ionization (APCI).

3. The method of claim 2, wherein said APCI is in negative ionization mode.

4. The method of claim 1, wherein said ionizing comprises electrospray ionization (ESI).

5. The method of claim 1, wherein said one or more ions comprise an ion with a mass to charge ratio (m/z) of 327.2 ±0.5.

6. The method of claim 1, wherein said one or more ions comprise an ion with a mass to charge ratio (m/z) of 301.2 ±0.5.

7. The method of claim 1, wherein said sample comprises human serum or plasma.

8. The method of claim 1, wherein said sample is subjected to a hydrolyzing agent prior to ionization.

9. The method of claim 8, wherein said hydrolyzing agent is an acid.

10. The method of claim 1, wherein said one or more omega-3 fatty acids is subjected to liquid/liquid extraction prior to ionization.

11. The method of claim 1, wherein said one or more omega-3 fatty acids is purified by liquid chromatography prior to ionization.

12. The method of claim 11, wherein said liquid chromatography comprises high performance liquid chromatography (HPLC).

* * * * *